United States Patent
Staley et al.

(10) Patent No.: US 10,232,130 B2
(45) Date of Patent: Mar. 19, 2019

(54) ANTI-RUN DRY MEMBRANE

(71) Applicant: Becton, Dickinson and Company, Franklin Lakes, NJ (US)

(72) Inventors: Shaun Staley, Sandy, UT (US); Weston O. Whitaker, Riverton, UT (US); Jon Larsen, Riverton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 211 days.

(21) Appl. No.: 15/078,709

(22) Filed: Mar. 23, 2016

(65) Prior Publication Data

US 2016/0279348 A1    Sep. 29, 2016

Related U.S. Application Data

(60) Provisional application No. 62/138,706, filed on Mar. 26, 2015.

(51) Int. Cl.
*A61M 5/38* (2006.01)
*A61M 5/14* (2006.01)
(Continued)

(52) U.S. Cl.
CPC ............ *A61M 5/38* (2013.01); *A61M 5/1411* (2013.01); *A61M 5/36* (2013.01); *A61M 5/44* (2013.01); *B01D 53/62* (2013.01); *A61M 5/385* (2013.01)

(58) Field of Classification Search
CPC ........ A61M 5/38; A61M 5/1411; A61M 5/36; A61M 5/44; A61M 5/385; B01D 53/62
(Continued)

(56) References Cited

U.S. PATENT DOCUMENTS 2,129,983 A    9/1938    Bacon
2,729,212 A    1/1956    Butler
(Continued)

FOREIGN PATENT DOCUMENTS

AU    771431 B2    3/2004
CA    2 460 251 A1    4/2003
(Continued)

OTHER PUBLICATIONS

Braun, Product Detail, the URL retrieved from http://www.bbraunoem-industrial.com/products/ details.cfm?prodid=B0843225&id-Caps &area=C, p. 1 (Apr. 12, 2005).
(Continued)

*Primary Examiner* — Manuel A Mendez
(74) *Attorney, Agent, or Firm* — Kirton & McConkie; Craig Metcalf; Kevin Stinger

(57) ABSTRACT

An intravenous delivery system may have a liquid source containing a liquid, tubing, and an anti-run-dry membrane positioned such that the liquid, flowing form the liquid source to the tubing, passes through the anti-run-dry membrane. The anti-run-dry membrane may have a plurality of pores through which the liquid flows, and may be formed of a hydrophilic material that resists passage of air through the pores. The intravenous delivery system may further have a bubble point raising component that raises the bubble point of the anti-run-dry membrane. The bubble point raising component may, in some embodiments, be a high surface energy coating or additive.

19 Claims, 8 Drawing Sheets

(51) Int. Cl.
*A61M 5/36* (2006.01)
*A61M 5/44* (2006.01)
*B01D 53/62* (2006.01)

(58) Field of Classification Search
USPC .................................. 604/507, 126, 103.1
See application file for complete search history.

(56) References Cited

U.S. PATENT DOCUMENTS

| | | | |
|---|---|---|---|
| 2,954,028 A | 9/1960 | Smith | |
| 3,030,954 A | 4/1962 | Thornton, Jr. | |
| 3,390,677 A | 7/1968 | Razimbaud | |
| 3,520,416 A * | 7/1970 | Keedwell | B01D 36/001 210/490 |
| 3,557,786 A | 1/1971 | Barr, Sr. et al. | |
| 3,631,654 A | 1/1972 | Riely et al. | |
| 3,722,697 A | 3/1973 | Burke et al. | |
| 3,744,492 A | 7/1973 | Leibinsohn | |
| 3,756,233 A | 9/1973 | Goldowsky | |
| 3,782,083 A | 1/1974 | Rosenberg | |
| 3,806,386 A | 4/1974 | Burke et al. | |
| 3,931,818 A | 1/1976 | Goldowsky | |
| 4,013,072 A | 3/1977 | Jess | |
| 4,034,754 A | 7/1977 | Virag | |
| 4,066,556 A | 1/1978 | Vaillancourt | |
| 4,113,627 A | 9/1978 | Leason | |
| 4,121,584 A | 10/1978 | Turner et al. | |
| 4,170,056 A | 10/1979 | Meyst et al. | |
| 4,173,222 A * | 11/1979 | Muetterties | A61M 5/1411 137/179 |
| 4,198,971 A | 4/1980 | Noiles | |
| 4,200,095 A * | 4/1980 | Reti | A61M 5/14 604/126 |
| 4,227,527 A | 10/1980 | De Frank et al. | |
| 4,243,032 A | 1/1981 | Howell | |
| 4,248,223 A | 2/1981 | Turner et al. | |
| 4,269,222 A | 5/1981 | Palti | |
| 4,276,170 A | 6/1981 | Vaillancourt | |
| 4,406,042 A | 9/1983 | McPhee | |
| 4,413,990 A | 11/1983 | Mittleman | |
| 4,428,743 A | 1/1984 | Heck | |
| 4,465,479 A | 8/1984 | Meisch | |
| 4,521,212 A | 6/1985 | Ruschke | |
| 4,548,600 A | 10/1985 | Ruschke | |
| 4,571,244 A | 2/1986 | Knighton | |
| 4,583,979 A | 4/1986 | Palti | |
| 4,589,171 A | 5/1986 | McGill | |
| 4,601,712 A | 7/1986 | Cole et al. | |
| 4,610,781 A | 9/1986 | Bilstad et al. | |
| 4,615,694 A | 10/1986 | Raines | |
| 4,625,494 A | 12/1986 | Iwatschenko et al. | |
| 4,685,912 A | 8/1987 | Jones | |
| 4,795,429 A | 1/1989 | Feldstein | |
| 4,812,293 A | 3/1989 | McLaurin et al. | |
| 4,842,588 A | 6/1989 | Jones | |
| 4,952,210 A | 8/1990 | Alchas | |
| 4,997,149 A | 3/1991 | Koch | |
| 5,102,400 A | 4/1992 | Leibinsohn | |
| 5,131,537 A | 7/1992 | Gonzales | |
| 5,188,588 A | 2/1993 | Schoendorfer et al. | |
| 5,195,987 A | 3/1993 | Karpiak | |
| 5,308,314 A | 5/1994 | Fukui et al. | |
| 5,308,333 A | 5/1994 | Skakoon | |
| 5,309,604 A | 5/1994 | Poulsen | |
| 5,389,082 A | 2/1995 | Baugues et al. | |
| 5,419,770 A | 5/1995 | Crass et al. | |
| 5,423,346 A | 6/1995 | Daoud | |
| 5,423,769 A | 6/1995 | Jonkman et al. | |
| 5,435,448 A | 7/1995 | Kempen | |
| 5,489,385 A | 2/1996 | Raabe et al. | |
| 5,542,160 A | 8/1996 | Arndt | |
| 5,681,294 A | 10/1997 | Osborne et al. | |
| 5,709,653 A * | 1/1998 | Leone | A61M 25/1027 604/103.01 |
| 5,735,826 A | 4/1998 | Richmond | |
| 5,776,109 A | 7/1998 | Urrutia | |
| 5,779,674 A | 7/1998 | Ford | |
| 5,836,923 A | 11/1998 | Mayer | |
| 5,851,202 A | 12/1998 | Carlsson | |
| 5,891,096 A | 4/1999 | Hyun et al. | |
| 5,899,665 A | 5/1999 | Makino et al. | |
| 5,902,281 A | 5/1999 | Kraus et al. | |
| 5,906,598 A | 5/1999 | Giesler et al. | |
| 6,015,119 A | 1/2000 | Starchevich | |
| 6,099,512 A | 8/2000 | Urrutia | |
| 6,103,119 A | 8/2000 | Clements et al. | |
| 6,106,504 A | 8/2000 | Urrutia | |
| 6,149,631 A | 11/2000 | Haydel, Jr. | |
| 6,213,986 B1 | 4/2001 | Darling, Jr. | |
| 6,224,578 B1 | 5/2001 | Davis et al. | |
| 6,261,267 B1 | 7/2001 | Chen | |
| 6,283,945 B1 | 9/2001 | Bierman | |
| 6,336,916 B1 | 1/2002 | Bormann et al. | |
| 6,503,225 B1 | 1/2003 | Kirsch et al. | |
| RE38,145 E | 6/2003 | Lynn | |
| D479,328 S | 9/2003 | Reynolds et al. | |
| 6,833,488 B2 | 12/2004 | Bucevschi et al. | |
| 7,160,087 B2 | 1/2007 | Fathallah et al. | |
| 7,722,577 B2 | 5/2010 | Miner | |
| 7,892,204 B2 | 2/2011 | Kraus | |
| 8,282,046 B2 | 10/2012 | Harding et al. | |
| 8,523,829 B2 | 9/2013 | Miner et al. | |
| 2002/0156431 A1 | 10/2002 | Feith et al. | |
| 2003/0220616 A1 | 11/2003 | Kraus | |
| 2004/0011749 A1 | 1/2004 | Hutchinson et al. | |
| 2004/0254542 A1 | 12/2004 | Sacco | |
| 2005/0059926 A1 | 3/2005 | Sage, Jr. et al. | |
| 2005/0171491 A1 | 8/2005 | Minh Miner et al. | |
| 2005/0249885 A1* | 11/2005 | Weis | G01N 27/404 427/443.2 |
| 2005/0273062 A1 | 12/2005 | Franksson et al. | |
| 2006/0188407 A1 | 8/2006 | Gable et al. | |
| 2006/0283544 A1 | 12/2006 | Mori et al. | |
| 2008/0097333 A1 | 4/2008 | Henning | |
| 2011/0276010 A1 | 11/2011 | Davis et al. | |
| 2012/0171403 A1* | 7/2012 | Dodge | C08J 9/365 428/36.1 |
| 2013/0224866 A1 | 8/2013 | Lurvey et al. | |
| 2013/0338588 A1 | 12/2013 | Grimm et al. | |
| 2013/0345658 A1 | 12/2013 | Browne et al. | |

FOREIGN PATENT DOCUMENTS

| | | |
|---|---|---|
| CN | 201 088 751 Y | 7/2008 |
| CN | 101 732 767 A | 6/2010 |
| CN | 203 107 819 U | 8/2013 |
| CN | 203107819 | 8/2013 |
| CN | 203 379 419 U | 1/2014 |
| DE | 41 42 625 A1 | 4/1993 |
| DE | 196 22 050 A1 | 12/1997 |
| EP | 0 001 114 A2 | 3/1979 |
| EP | 0 195 310 A1 | 9/1986 |
| EP | 0 229 354 A2 | 7/1987 |
| EP | 0 788 824 A3 | 11/1998 |
| EP | 1 181 065 B1 | 7/2003 |
| EP | 2 500 051 A1 | 9/2012 |
| FR | 2 160 821 A1 | 7/1973 |
| GB | 2 044 620 A | 10/1980 |
| JP | H10-127778 A | 5/1998 |
| JP | 2000-014745 A | 1/2000 |
| JP | 2000-229126 A | 8/2000 |
| WO | 96/29104 A1 | 9/1996 |
| WO | 99/22787 A1 | 5/1999 |
| WO | 00/66200 A1 | 11/2000 |
| WO | 01/41844 A1 | 6/2001 |
| WO | 03/028525 A2 | 4/2003 |
| WO | 2005/104776 A2 | 11/2005 |
| WO | 2005/118051 A2 | 12/2005 |
| WO | 2006/083359 A2 | 8/2006 |
| WO | 2007/079049 A2 | 7/2007 |
| WO | 2008/027157 A1 | 3/2008 |
| WO | 2009/046182 A1 | 4/2009 |
| WO | 2010/030602 | 3/2010 |

(56) References Cited

FOREIGN PATENT DOCUMENTS

| WO | 2010/030602 A1 | 3/2010 |
| WO | 2011/139517 | 11/2011 |
| WO | 2011/139517 A1 | 11/2011 |
| WO | 2013/070337 A1 | 5/2013 |
| WO | 2013/188103 | 12/2013 |
| WO | 2013/188103 A1 | 12/2013 |

OTHER PUBLICATIONS

Shift Labs, DripAssist Infusion Rate Monitor, http://www.shiftlabs.com/dripassist-human-health, pp. 1-5, Apr. 3, 2017.

* cited by examiner

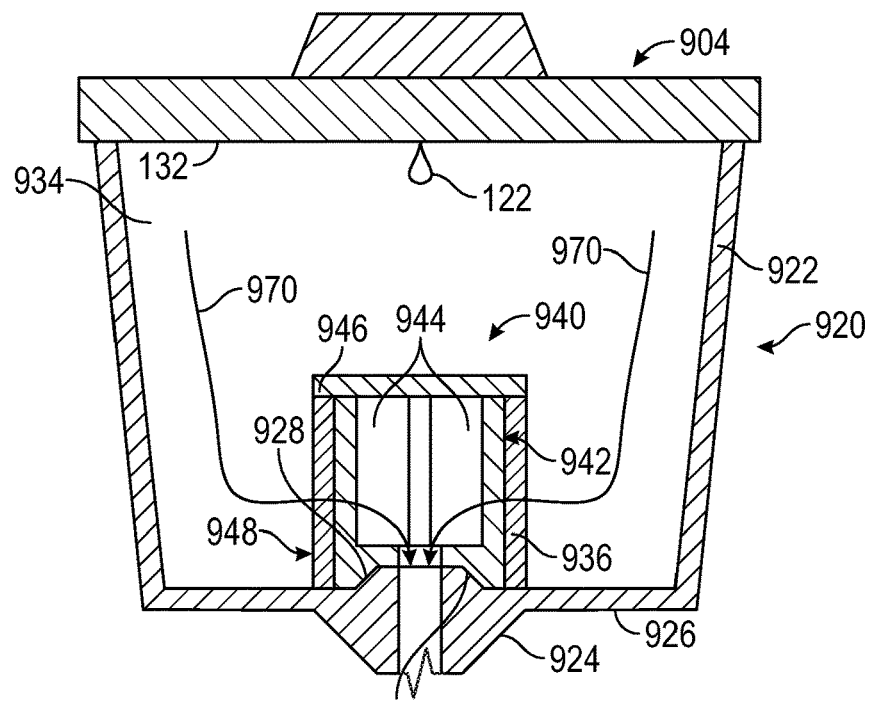
FIG. 9
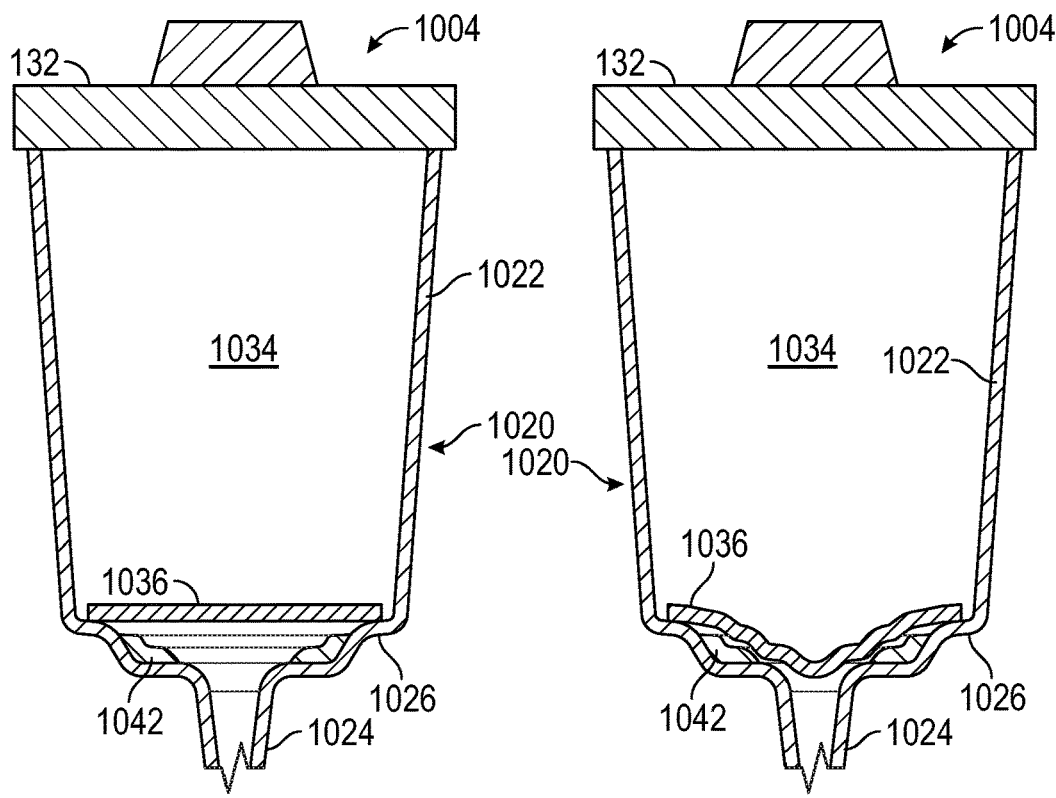
FIG. 10A
FIG. 10B

ANTI-RUN DRY MEMBRANE

RELATED APPLICATIONS

This application claims priority to U.S. Provisional Patent Application Ser. No. 62/138,706, filed Mar. 26, 2015, and entitled IMPROVED ANTI-RUN DRY MEMBRANE, which is incorporated herein in its entirety.

BACKGROUND

The present invention is generally directed to systems and methods for intravenous ("IV") delivery, by which fluids can be administered directly to a patient. More particularly, the present invention is directed to anti-run-dry (ARD) membranes that can be included within intravenous delivery systems to restrict flow of air into the tubing of the intravenous delivery system. An intravenous delivery system according to the invention is used broadly herein to describe components used to deliver the fluid to the patient, for use in arterial, intravenous, intravascular, peritoneal, and/or nonvascular administration of fluid. Of course, one of skill in the art may use an intravenous delivery system to administer fluids to other locations within a patient's body.

One common method of administering fluids into a patient's blood flow is through an intravenous delivery system. In many common implementations, an intravenous delivery system may include a liquid source such as a liquid bag, a drip chamber used to determine the flow rate of fluid from the liquid bag, tubing for providing a connection between the liquid bag and the patient, and an intravenous access unit, such as a catheter that may be positioned intravenously in a patient. An intravenous delivery system may also include a Y-connector that allows for the piggybacking of intravenous delivery systems and for the administration of medicine from a syringe into the tubing of the intravenous delivery system.

It is a generally good practice to remove air from intravenous delivery systems that access a patient's blood flow. While this concern is critical when accessing arterial blood, it is also a concern when accessing the venous side. Specifically, if air bubbles are allowed to enter a patient's blood stream while receiving the intravenous administration of fluids, the air bubbles can form an air embolism and cause serious injury to a patient.

Normally, in a majority of adults, the right atrium and the left atrium are completely separated from each other so that the blood and air bubbles are moved from the right atrium, to the right ventricle, and then to the lungs where the air bubbles may be safely vented. The bubble free blood is then returned to the left atrium, where the blood is moved to the left ventricle and then sent throughout the body.

However, in infants and in a small portion of the adult population, the right atrium and left atrium are not completely separated. Consequently, air bubbles can move directly from the right atrium into the left atrium and then be dispersed throughout the body. As a result, these air bubbles may cause strokes, tissue damage, and/or death. Therefore, it is important to prevent air bubbles from entering a patient's blood stream.

In spite of the importance of removing air bubbles while priming an intravenous delivery system for use in the intravenous administration of fluids, the complete removal of air bubbles can be a time consuming process. The process may also lead to contamination of the intravenous delivery system by inadvertently touching a sterile end of the intravenous delivery system. Typically, when an intravenous delivery system is primed, a clamp is closed to prevent fluid from moving from a drip chamber through the tubing. The intravenous delivery system may then be attached to an IV bag or bottle. Once attached, the drip chamber, which is typically made of a clear flexible plastic, may be squeezed to draw the fluid out of the IV bag or bottle and into the drip chamber. The drip chamber may be allowed to fill about ¼ to ½ full when the clamp is opened to allow fluid to flow through the tube to an end of the intravenous delivery system.

This initial process, however, typically traps air in tubing which must be removed. For example, the flow of the fluid through the tubing of the intravenous delivery system may be turbulent and can entrap air within the tube as the boundary layer between the fluid and the tubing is sheared. The flow rate out of the drip chamber may be higher than the flow rate of fluid entering the drip chamber. This can cause a bubble ladder to form as air is sucked from the drip chamber into the tubing.

Additionally, air bubbles may be generated as drops of fluid strike the surface of the pool of fluid within the drip chamber. These air bubbles can be pulled into the tubing of the IV set from the drip chamber. This problem may be aggravated in pediatric applications where the drip orifice may be smaller, which may result in increased turbulence.

To remove air bubbles from the intravenous delivery system, fluid from the IV bag or bottle may be allowed to flow through the tubing while an attendant taps the tubing to encourage the air bubbles out the end of the intravenous delivery system. As the fluid is allowed to flow out of the intravenous delivery system to clear air bubbles from the tubing, the fluid may be allowed to flow into a waste basket or other receptacle. During this procedure, the end of the tubing may contact the waste basket or be touched by the attendant and thus, become contaminated. An additional shortcoming of this debubbling process is that it requires attention and time that could have been used to perform other tasks that may be valuable to the patient.

Another debubbling method is to directly remove air bubbles from the intravenous delivery system. More specifically, if the intravenous delivery system includes a Y-connector, air bubbles may be removed at the Y-connector by a syringe. This method still requires additional time and attention, and may also carry risk of contamination of the liquid to be delivered.

To address the difficulties of removing bubbles from an intravenous delivery system, various prior art intravenous delivery systems have employed a membrane for filtering air from the fluid as it flows through the intravenous delivery system. For example, oftentimes a membrane may be placed in the bottom of the drip chamber so that fluid flowing out of the drip chamber must pass through the membrane. The membrane can be configured to allow the passage of fluid while blocking the passage of air. In this way, bubbles are prevented from passing into the tubing leading to the patient. Similarly, a membrane can be included in the connector that couples the tubing to a catheter to block any air present in the tubing from passing into the patient's vasculature.

The use of air filtering membranes in these prior art intravenous delivery system designs have been beneficial. However, even with the use of these membranes, various drawbacks still exist. For example, if a fluid bag is allowed to empty, all of the fluid within the intravenous delivery system will pass through the intravenous delivery system and into the patient, leaving the intravenous delivery system full of air. Once this occurs, the intravenous delivery system will have to be re-primed to remove the air from the intravenous delivery system before a new fluid bag can be administered. To avoid having to re-prime the intravenous delivery system, clinicians will therefore have to be present as a fluid bag is emptying to ensure that the fluid bag can be replaced before the drip chamber empties.

Also, if the clinician does not notice that air has entered into the tubing, he or she may fail to re-prime the intravenous delivery system when connecting a new fluid bag. This may result in air passing into the patient once the new fluid bag is administered. Further, if the membrane will not support a sufficiently lengthy column of fluid, the air filtration capabilities of the membrane may be overcome by continued flow of fluid into the tubing downstream of the membrane.

BRIEF SUMMARY OF THE INVENTION

Embodiments of the present invention are generally directed to an intravenous delivery system with a bubble point raising component that enhances the operation of an anti-run-dry membrane. The intravenous delivery system may have a liquid source containing a liquid to be delivered to a patient, a drip unit containing the anti-run-dry membrane, tubing, and the bubble point raising component. The tubing may have a first end connectable to the liquid source, and a second end connectable to a vent cap and/or an intravenous delivery unit.

The anti-run-dry membrane may be formed of a hydrophilic material, and may have a roughened surface that increases the bubble point of the anti-run-dry membrane. The anti-run-dry membrane may have a plurality of pores that permit the liquid to flow through the anti-run-dry membrane, while resisting passage of air through the anti-run-dry membrane. The pores may be relatively small, for example, less than about 3 micrometers in effective diameter. Further, the anti-run-dry membrane may have a relatively small thickness, for example, less than about 90 micrometers.

The bubble point raising component may include a high surface energy additive that is added to the base material of the anti-run-dry membrane during manufacturing of the anti-run-dry membrane to increase the surface energy of the anti-run-dry membrane. Additionally or alternatively, the bubble point raising component may include a high surface energy coating applied to the exterior of the anti-run-dry membrane after formation of the anti-run-dry membrane. Additionally or alternatively, the bubble point raising component may be a cooling device applied to the liquid that will flow through the anti-run-dry membrane to cool the liquid, thereby raising the bubble point of the anti-run-dry membrane.

The combination of the geometry of the anti-run-dry membrane and the operation of the bubble point raising component may tend to restrict flow of the liquid through the anti-run-dry membrane. In order to compensate for this and ensure that the anti-run-dry membrane provides an adequate flow rate of the liquid, the anti-run-dry membrane may have a nonplanar shape that effectively increases the surface area of the anti-run-dry membrane through which the liquid is able to flow. Such nonplanar shapes may include, but need not be limited to, tubular shapes, domed shapes, and/or folded or pleated shapes. A folded shape may include at least one fold between two adjacent surfaces of the anti-run-dry membrane, with the fold defining an acute angle between the adjacent surfaces.

According to one method, an intravenous delivery system may be used by, first, connecting the various components of the intravenous delivery system together. This may entail connecting the liquid source, drip unit, and tubing together. The intravenous delivery system may then be primed by gravity feeding liquid from the liquid source to the vent cap through the tubing. In response to priming the intravenous delivery system, the vent cap may vent air out of the intravenous delivery system. The intravenous access unit may then be connected to the second end of the tubing and used to deliver the liquid to the patient.

The flow of liquid to the patient may be stopped, for example, due to depletion of the liquid in the liquid source. A column of the liquid may then develop below the anti-run-dry membrane, in the lower part of the drip unit and in the tubing, proximate the first end. The bubble point raising component may serve to raise the bubble point of the anti-run-dry membrane to a level sufficient to enable the anti-run-dry membrane to support the liquid column without permitting entry of a significant quantity of air into the column.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

FIG. 9 is a front elevation, section view of a drip unit according to yet another alternative embodiment;

FIGS. 10A and 10B are front elevation, section views of a drip unit according to still another alternative embodiment, prior to and after shaping of the anti-run-dry membrane, respectively.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
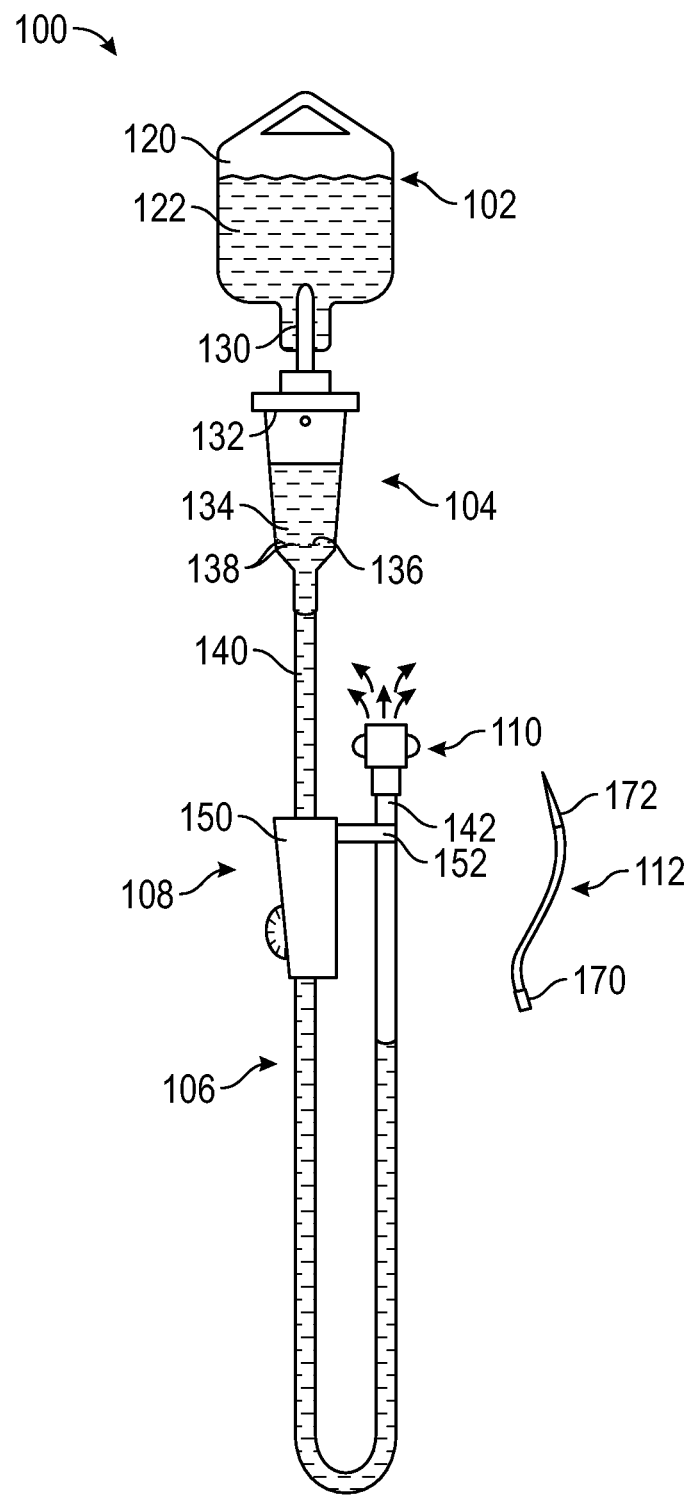
FIG. 1 is a front elevation view of an intravenous delivery system according to one embodiment.

Referring to FIG. 1, a front elevation view illustrates an intravenous delivery system 100 according to one embodiment. As shown, the intravenous delivery system 100 may have a number of components, which may include a liquid source 102, a drip unit 104, tubing 106 a retention unit 108, a vent cap 110, and an intravenous access unit 112. The manner in which these components are illustrated in FIG. 1 is merely exemplary; those of skill in the art will recognize that a wide variety of intravenous delivery systems exist. Thus, the various components the intravenous delivery system 100 may be omitted, replaced, and/or supplemented with components different from those illustrated.

The liquid source 102 may have a container containing a liquid 122 to be delivered intravenously to a patient. The liquid source 102 may, for example, have a bag 20, which may be formed of a translucent, flexible polymer or the like. The bag 120 may thus have a baglike configuration. The bag 120 may be shaped to contain the liquid 122.

The drip unit 104 may be designed to receive the liquid 122 from the bag 120 in a measured rate, for example, as a series of drips occurring at a predictable, consistent rate. The drip unit 104 may be positioned below the bag 120 so as to receive the liquid 122 via gravity feed. The drip unit 104 may have a receiving device 130 that receives the liquid 122 from the liquid source 102, a drip feature 132 that determines the rate at which the liquid 122 is received by the drip unit 104, and a drip chamber 134 in which the liquid 122 is collected. An anti-run-dry membrane may be positioned within the drip chamber 134 to enable a fluid column of significant length to be maintained within the tubing 106 after cessation of flow of the liquid 122 into the tubing 106, without permitting significant air to flow into the tubing 106 through the anti-run-dry membrane 136.

The tubing 106 may be standard medical grade tubing. The tubing 106 may be formed of a flexible, translucent material such as a silicone rubber. The tubing 106 may have a first end 140 and a second end 142. The first end 140 may be coupled to the drip unit 104, and the second end 142 may be coupled to the vent cap 110, such that the liquid 122 flows from the drip unit 104 to the vent cap 110, through the tubing 106.

The retention unit 108 may be used to retain various other components of the intravenous delivery system 100. As shown, the retention unit 108 may have a main body 150 and an extension 152. Generally, the tubing 106 may be connected to the main body 150 proximate the first end 140, and to the extension 152 proximate the second end 142. Various racks, brackets, and/or other features may be used in addition to or in place of the retention unit 108.

The vent cap 110 may be coupled to the second end 142 of the tubing 106. The vent cap 110 may have a vent, such as a hydrophobic membrane that is substantially permeable to air, but not to the liquid 122. Thus, air from within the vent cap 110 can be vented from the intravenous delivery system 100, with limited leakage of the liquid 122 from the intravenous delivery system 100.

The intravenous access unit 112 may be used to supply the liquid 122 to the vascular system of the patient. The intravenous access unit 112 may have a first end 170 and an access end 172. The first end 170 may be connectable to the second end 142 of the tubing 106 in place of the vent cap 110. Thus, when the intravenous delivery system 100 is fully primed, the intravenous access unit 112 may be coupled to the second end 142 of the tubing 106 in place of the vent cap 110. In alternative embodiments (not shown), various connectors such as Y-adapters may be used to connect the first end 170 of the intravenous access unit 112 to the tubing 106 without detaching the vent cap 110 from the second end 142 of the tubing 106.

The intravenous delivery system 100 may be primed by connecting the components (except for the intravenous access unit 112) together as illustrated in FIG. 1, and then allowing the liquid 122 to gravity feed through the drip unit 104 and the tubing 106 into the vent cap 110. If desired, the drip unit 104 may be squeezed or otherwise pressurized to expedite flow of the liquid 122 through the tubing 106.

As the liquid 122 flows through the tubing 106, air may become entrained in the liquid 122. This air may move from the first end 140 of the tubing 106, toward the second end 142 of the tubing 106, along with the column of liquid 122. This entrained air may gather into bubbles proximate the second end 142 of the tubing 106. The vent cap 110 may be designed to receive the liquid 122 to permit such air bubbles to be vented from the intravenous delivery system 100 through the vent cap 110.

Once the liquid 122 stops flowing into the liquid 122, for example, due to depletion of the liquid 122 in the liquid source 102, the anti-run-dry membrane 136 may act to restrict motion of air into the tubing 106. The anti-run-dry membrane 136 may have a plurality of pores 138, each of which has a size that causes the formation of a meniscus of the liquid 122 underneath the anti-run-dry membrane 136. Each meniscus may, via capillary action, contribute to the support of a column of the liquid 122 in the tubing 106. The anti-run-dry membrane 136 may be designed to facilitate support of a column of the liquid 122 of significant length before permitting air to enter the column. The longer the column that can be supported, the more robust the intravenous delivery system 100 will be to different operational conditions.

In order to enhance the length of the column of the liquid 122 that can be supported by the anti-run-dry membrane 136, the intravenous delivery system 100 may also include a bubble point raising component. This is not shown in FIG. 1; however, various bubble point raising components will be shown and described in connection with the following figures. Generally, a "bubble point raising component" may be any feature of an intravenous delivery system that increases the bubble point of an anti-run-dry membrane. The "bubble point" is the pressure at which a continuous stream of bubbles is initially seen downstream of a wetted filter under gas pressure. Raising the bubble point of the anti-run-dry membrane 136 will increase the length of the column of drip feature 132 that can be supported by the anti-run-dry membrane 136 without entry of a significant quantity of air into the column. Some related principles will be shown and described in connection with FIG. 2.

Figure 2:
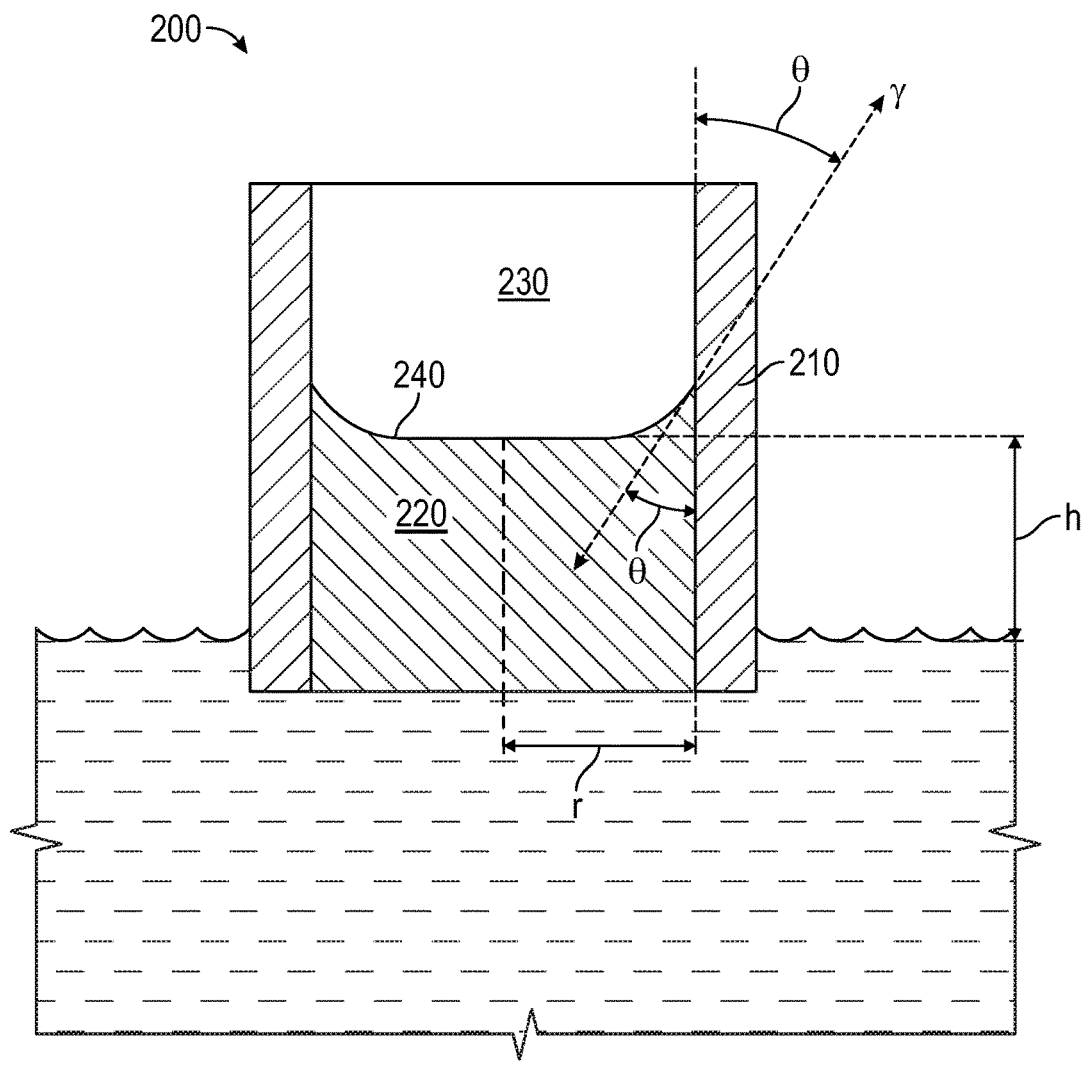
FIG. 2 is a diagram of a portion of tubing, generally, illustrating the maintenance of a fluid column within the tubing.

Referring to FIG. 2, a diagram 200 of a portion of tube wall 210, generally, illustrates the maintenance of a column of the liquid 220 within the tube wall 210. The tube wall 210 of FIG. 2 is representative of any structure that defines a liquid/gas interface, such as an individual pore of a membrane (such as one of the pores 138 of the anti-run-dry membrane of FIG. 1). The tube wall 210 (or pores 138) may have a radius r, as shown. The column of the liquid 220 to be supported within the tube wall 210 may have a height h, as also shown.

As shown, a meniscus 240 may exist at the boundary between the liquid 220 and the air 230 upstream of the liquid 220. The tube wall 210 may be formed of a hydrophilic material; thus, the meniscus 240 may curve upward at the ends, where the meniscus 240 meets the tube wall 210. The meniscus 240 may thus form a contact angle θ relative to the tube wall 210. The surface tension force exerted by the meniscus 240 against the tube wall 210 is parallel to the contact angle of the meniscus 240 to the liquid 220, and is therefore indicated by a vector labeled γ. The height h of the column of the liquid 122 that can be supported may be obtained by the equation:

$$h = \frac{2\gamma\cos\theta}{\rho g r}$$

where ρ is the density of the liquid 122, and g is the gravitational constant.

From the equation referenced above, it can be seen that h may be increased by increasing γ and/or by reducing θ. These may optionally be accomplished in various ways according to the present disclosure. In some embodiments, γ may be increased, and θ may be decreased, by increasing the surface energy of the material of the tube wall 210. With reference again to the embodiment of FIG. 1, this may entail increasing the surface energy of the anti-run-dry membrane 136 within the drip unit 104.

Increasing the surface energy of the anti-run-dry membrane 136 may be accomplished, for example, by applying a coating or an additive to the anti-run-dry membrane 136. The coating or additive may include a material with a higher surface energy than that of the base material used to form the anti-run-dry membrane 136. In the case of the additive, a high surface energy additive may be applied during manufacture of the anti-run-dry membrane 136, for example by mixing the additive with the base material of which the anti-run-dry membrane 136 is to be formed, prior to formation of the anti-run-dry membrane 136 in its final shape. Various known mixing methods may be used, and may optionally involve the use of chemical bonds. In the case of a coating, a high surface energy coating may be applied to the exterior of the anti-run-dry membrane 136 after the anti-run-dry membrane 136 has been formed. This may be carried out through the use of any known coating method.

Use of a high surface energy additive or coating represents only some of many possible ways of increasing the bubble point of the anti-run-dry membrane 136. Other embodiments will be described subsequently. A generalized method of using the intravenous delivery system 100 will be shown and described in connection with FIG. 3.

Figure 3:
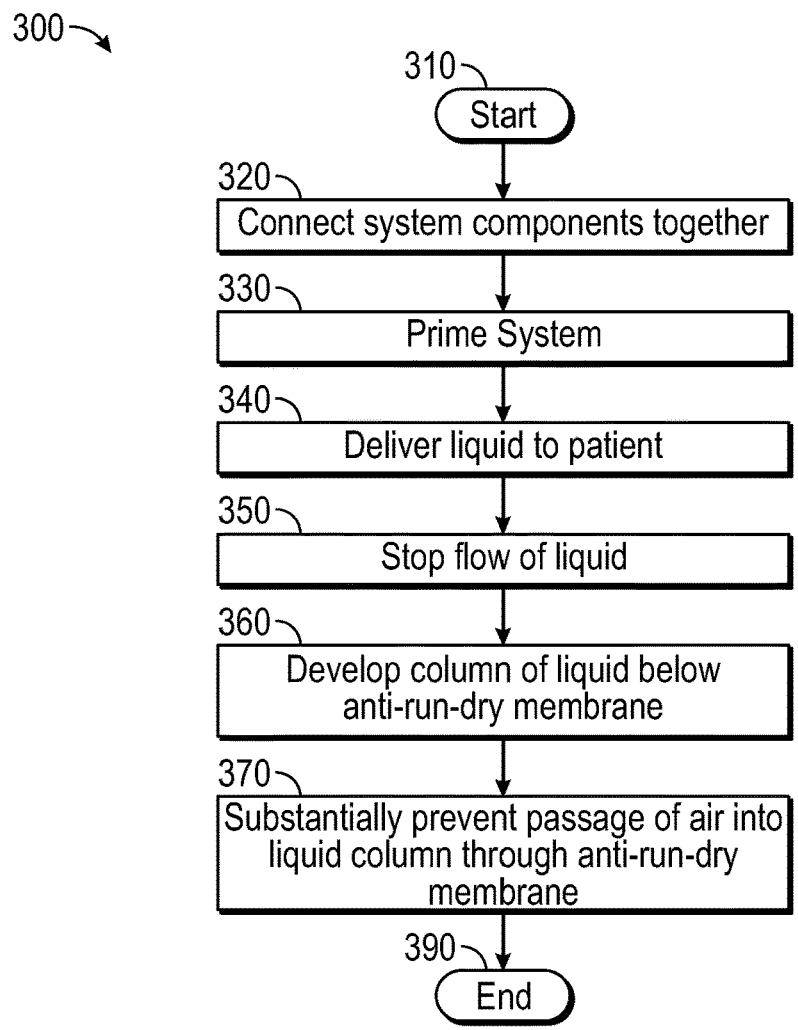
FIG. 3 is a flowchart diagram illustrating a method of using an intravenous delivery system, according to one embodiment.

Referring to FIG. 3, a flowchart diagram illustrates a method 300 of preparing an intravenous delivery system for use, according to one embodiment. The method 300 will be described with reference to the intravenous delivery system 100 of FIG. 1. However, those of skill in the art will recognize that the method 300 may be carried out with different intravenous delivery systems. Similarly, the intravenous delivery system 100 may be prepared for use through the use of methods other than that of FIG. 3.

The method 300 may start 310 with a step 320 in which the various components of the intravenous delivery system 100 are connected together, except for the intravenous access unit 112. Some of the components of the intravenous delivery system 100, such as the tubing 106 and the vent cap 110, may be packaged, sold and/or provided to the end user in a condition in which they are already connected together. The step 320 may only include interconnection of components of the intravenous delivery system 100 that have not already been connected together.

In a step 330, the intravenous delivery system 100 may be primed. As indicated previously, this may be done by simply allowing the liquid 122 to flow through the tubing 106 to the vent cap 110 via gravity, or by squeezing or otherwise pressuring the drip unit 104.

In a step 340, the liquid 122 may be delivered to the patient, for example, through the use of the intravenous access unit 112. In a step 350, delivery of the liquid 122 may be stopped. This may occur due to depletion of the liquid 122 within the liquid source 102, and/or various actions taken by clinicians to stop the flow of the liquid 122 through the intravenous delivery system 100, such as detachment of the liquid source 102 from the remainder of the intravenous delivery system 100.

In a step 360, a column of the liquid 122 may develop below the anti-run-dry membrane 136. This may occur as residual amounts of the liquid 122 (for example, from the portion of the drip chamber 134 above the anti-run-dry membrane 136) pass through the anti-run-dry membrane 136 and into the tubing 106. It may be desirable to prevent air entry into the column so that the intravenous delivery system 100 can be used for further delivery of the liquid 122 (or a different liquid) to the patient, without the need to repeat the step 330 by re-priming the intravenous delivery system 100.

Hence, in a step 370, the bubble point raising component may be used to substantially prevent passage of air into the column of the liquid 122 through the anti-run-dry membrane 136. In this disclosure, the phrases "substantially prevent passage of air" and "resist passage of air" refer to systems and methods by which air entry in the column is restricted to levels safe enough to permit delivery of the liquid column to a patient through the further use of the intravenous delivery system. The method 300 may then end 390.

As mentioned previously, many different types of bubble point raising components may be used within the scope of the present disclosure. Aside from raising the surface energy of the anti-run-dry membrane 136, other bubble point raising components may include components designed to modify other properties of the anti-run-dry membrane 136 and/or the liquid 122. In some embodiments, the surface roughness of the anti-run-dry membrane 136 may be increased to decrease the apparent contact angle θ, per Wenzel's equation, between the anti-run-dry membrane 136 and the liquid 122. In other embodiments, the cleanliness and/or homogeneity of the anti-run-dry membrane 136 may be enhanced. In yet other embodiments, the temperature of the liquid 122 may be reduced. A bubble point raising component according to the present disclosure may be designed to accomplish any of these objectives in addition to or in place of increasing the surface energy of the anti-run-dry membrane 136. One example of a bubble point raising component that cools the liquid 122 will be shown and described in connection with FIG. 4.

Figure 4:
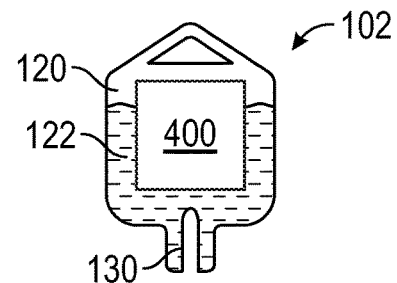
FIG. 4 is a front elevation view of the liquid source of FIG. 1, with a bubble point raising component in the form of a cooling device.

Referring to FIG. 4, a front elevation view illustrates the liquid source 102 of FIG. 1, with a bubble point raising component in the form of a cooling device 400. The cooling device 400 may be positioned on or near the liquid source 102, and may absorb heat from the liquid 122. The cooling device 400 may thus be a container of a cooled liquid, solid, or gas, such as an ice pack, or the like. Additionally or alternatively, the cooling device 400 may use the refrigeration cycle to continuously receive heat from the liquid 122. For example, the cooling device 400 may include a compressor, an expansion valve, an evaporator, and/or a condenser that are interconnected by conduits. A refrigerant of any known type may circulate through the conduits to continuously convey heat from the liquid 122 within the liquid source 102 to a heat sink, such as the ambient air.

The cooling device 400 may enhanced the ability of the anti-run-dry membrane 136 to resist moisture pass-through by strengthening the adherence of the liquid 122 to the anti-run-dry membrane 136. This may be done by cooling the liquid 122, which increases the surface tension γ.

Additionally or alternatively, the pores 138 of the anti-run-dry membrane 136 may be made relatively small. In some embodiments, the pores 138 of the anti-run-dry membrane 136 may have a size of less than 3 micrometers (i.e., a diameter of less than 3 micrometers, in the case of circular pores). Yet further, the pores 138 may each have a size of less than 2.5 micrometers, less than 2 micrometers, or even less than 1.5 micrometers. Further, the anti-run-dry membrane 136 may have a relatively small thickness. In some embodiments, the anti-run-dry membrane 136 may have a thickness of less than 90 micrometers. Yet further, the anti-run-dry membrane 136 may have a thickness of less than 75 micrometers, less than 60 micrometers, or even less than 45 micrometers.

Such small pore sizes may tend to limit the flow rate of the liquid 122 through the anti-run-dry membrane 136. Thus, it may be desirable to compensate for this by increasing the surface are of the anti-run-dry membrane 136. Specifically, in various embodiments that will be shown and described subsequently, an anti-run-dry membrane may have a nonplanar shape, at least during flow of the liquid 122 through the anti-run-dry membrane. Such nonplanar shapes may include, but are not limited to domed shapes, folded or pleated shapes, cylindrical shapes, and combinations thereof.

Figure 5A:
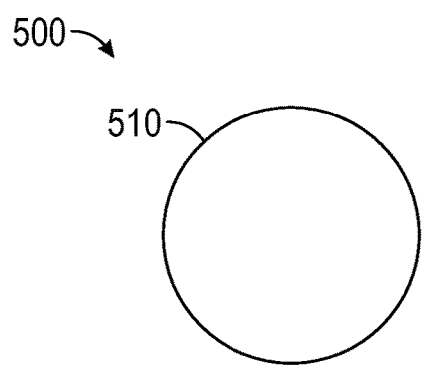
FIGS. 5A and 5B are plan and front elevation views, respectively, of an anti-run-dry membrane according to one embodiment.
Figure 5B:
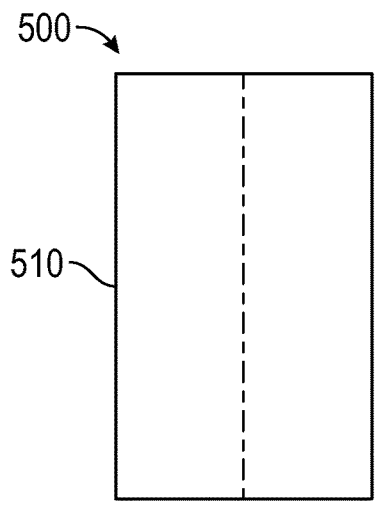

Referring to FIGS. 5A and 5B, plan and front elevation views, respectively, illustrate an anti-run-dry membrane 500 according to one embodiment. As shown, the anti-run-dry membrane 500 may have a tubular wall 510 that defines a generally tubular shape. The generally tubular shape may provide for a larger surface area within a given form factor. In some examples, the anti-run-dry membrane 500 may be oriented parallel to the flow of the liquid 122 so that the anti-run-dry membrane 500 fits within a space having a relatively compact cross sectional area.

Figure 5C:
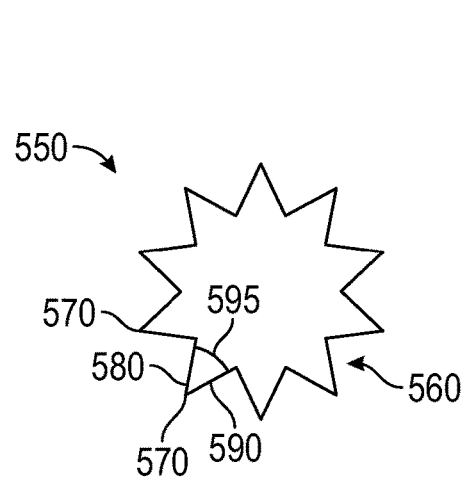
FIGS. 5C and 5D are plan and front elevation views, respectively, of an anti-run-dry membrane according to another embodiment.
Figure 5D:
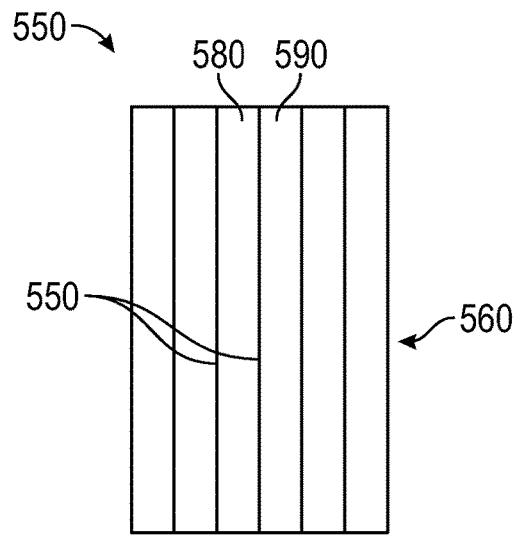

Referring to FIGS. 5C and 5D, plan and front elevation views, respectively, illustrate an anti-run-dry membrane 550 according to another embodiment. As shown, the anti-run-dry membrane 550 may have a tubular wall 510 that defines a generally tubular shape generally similar to that of the anti-run-dry membrane 500 of FIGS. 5A and 5B. However, in addition to a generally tubular shape, the tubular wall 560 may have a plurality of folds 570 that further augment the surface area of the tubular wall 560. Each of the fold 570 may provide an intersection between a first membrane surface 580 and a second membrane surface 590, which intersection may optionally occur at an acute angle 595. Like the anti-run-dry membrane 500, the anti-run-dry membrane 550 may be oriented parallel to the flow of the liquid 122 so that the anti-run-dry membrane 550 fits within a space having a relatively compact cross sectional area.

The anti-run-dry membrane 500 and the anti-run-dry membrane 550 may have pores or pores like the pores 138 of the anti-run-dry membrane 136 of FIG. 1. The anti-run-dry membrane 500 and the anti-run-dry membrane 550 are merely examples of nonplanar shapes that can be used in the construction of an anti-run-dry membrane according to the present disclosure. Such nonplanar membranes may be supported and used in various components of an intravenous delivery system. In some examples, such a nonplanar anti-run-dry membrane may be positioned within a drip unit, such as the drip unit 104 of FIG. 1. FIGS. 6-11 illustrate various different drip unit configurations that may alternatively be used to house a nonplanar anti-run-dry membrane.

Figure 6:
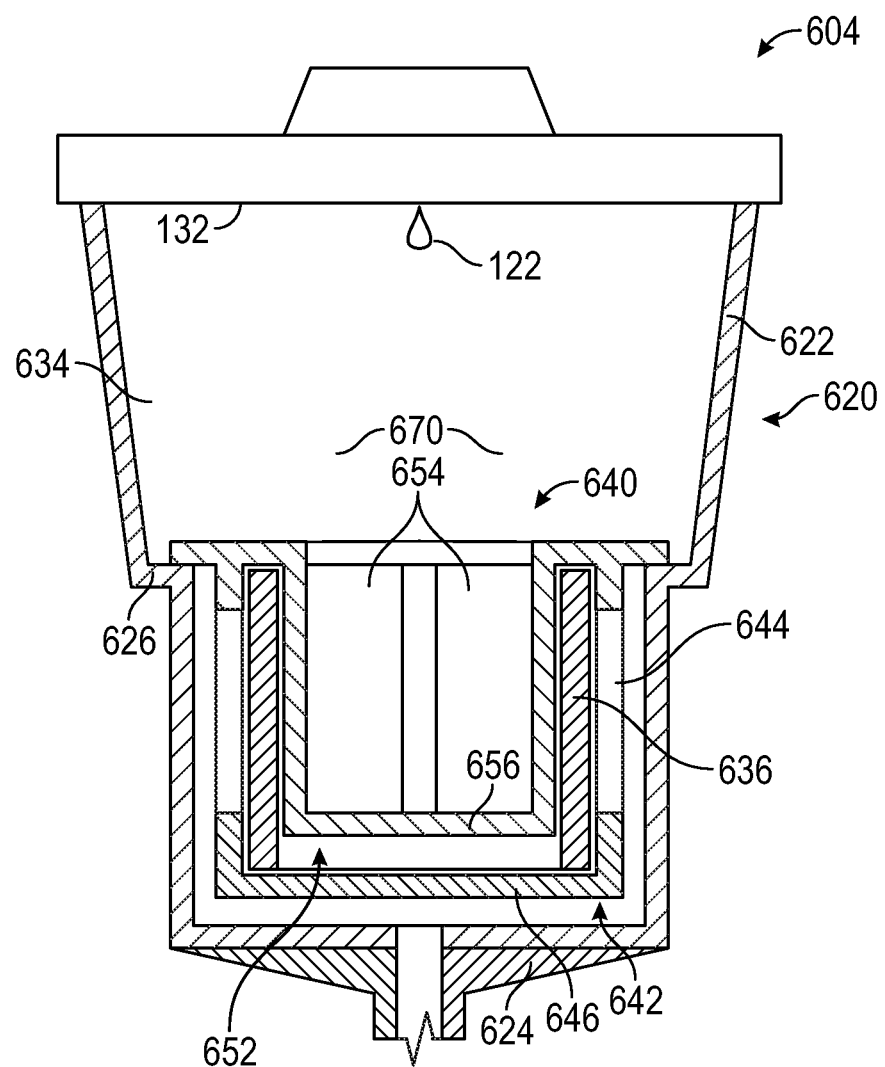
FIG. 6 is a front elevation, section view of a drip unit according to one embodiment.

Referring to FIG. 6, a front elevation, section view illustrates a drip unit 604 according to one embodiment. The drip unit 604 may have a drip feature 132 like that of FIG. 1. The drip unit 604 may have an exterior wall 620 that generally defines a drip chamber 634 to contain the liquid 122. The exterior wall 620 may have a peripheral portion 622 with a generally tubular and/or frustoconical shape, and a tubing interface 624 positioned below the peripheral portion 622 and designed to be connected to the first end 140 of the tubing 106. The exterior wall 620 may have a shelf 626 positioned to define a boundary between the peripheral portion 622 and the tubing interface 624.

The drip unit 604 of FIG. 6 may contain an anti-run-dry membrane 636 with a generally tubular shape, which may have a configuration similar to that of the anti-run-dry membrane 500 of FIGS. 5A and 5B and/or that of the anti-run-dry membrane 550 of FIGS. 5C and 5D. The anti-run-dry membrane 636 may be retained in a cartridge 640, which may be formed separately from the exterior wall 620 and installed to rest on the shelf 626 of the exterior wall 620. The cartridge 640 may have an outer wall 642 with a plurality of slots 644 extending longitudinally along its length. The outer wall 642 may have a solid base 646 that is substantially impermeable to the liquid 122. Alternatively, the solid base 646 may be replaced with an anti-run-dry membrane (not shown) like that of the anti-run-dry membrane 636, but with a shape that has a generally circular periphery (such as a generally circular or domed shape).

The cartridge 640 may also have an inner wall 652 with a plurality of slots 654 extending longitudinally along its length. The inner wall 652 may have a solid base 656 that is substantially impermeable to the liquid 122. Alternatively, like the solid base 646, the solid base 656 may be replaced with an anti-run-dry membrane (not shown) like that of the anti-run-dry membrane 636, but with a shape that has a generally circular periphery (such as a generally circular or domed shape).

In the configuration shown in FIG. 6, the liquid 122 may flow through the cartridge 640 to reach the tubing 106 via the tubing interface 624. Flow of the liquid 122 may be as indicated by the arrows 670. The liquid 122 may flow from the drip chamber 634, downward through the top of the cartridge 640 to reach the interior of the cartridge 640. Then, the liquid 122 may flow through the slots 654 of the inner wall 652 to reach the anti-run-dry membrane 636. The liquid 122 may then pass through the anti-run-dry membrane 636, and out of the cartridge 640 through the slots 644 of the outer wall 642.

The anti-run-dry membrane 636 may operate to trap any air in the interior of the cartridge 640, rather than allowing it to pass into the tubing interface 624. Conversely, after the liquid 122 has passed through the anti-run-dry membrane 636, the liquid 122 may continue moving downward into the tubing interface 624, and thence into the tubing 106.

In alternative embodiments, rather than having an anti-run-dry disposed within a cartridge in a drip unit, a two-piece drip unit may be used. One piece of the drip unit may effectively act as a cartridge by containing an anti-run-dry membrane. One example of such an embodiment will be shown and described in connection with FIG. 7.

Figure 7:
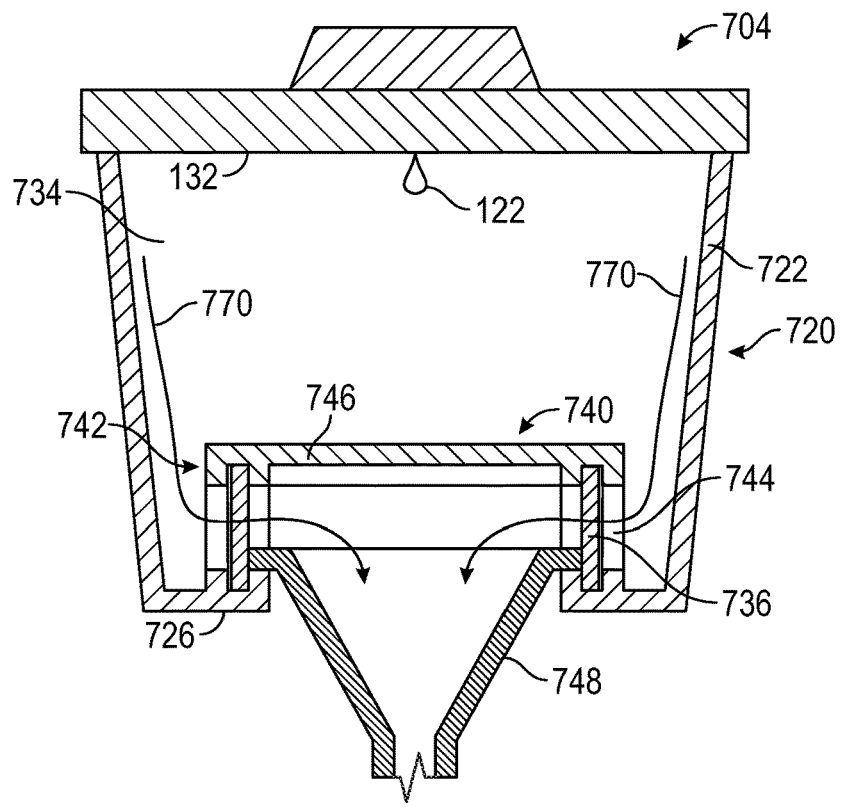
FIG. 7 is a front elevation, section view of a drip unit according to one alternative embodiment.

Referring to FIG. 7, a front elevation, section view illustrates a drip unit 704 according to one alternative embodiment. The drip unit 704 may have a drip feature 132 like that of FIG. 1. The drip unit 704 may have an exterior wall 720 that generally defines a drip chamber 734 to contain the liquid 122. The exterior wall 720 may have a peripheral portion 722 with a generally tubular and/or frustoconical shape, and a shelf 726 positioned at the bottom of the peripheral portion 722. The shelf 726 may define an opening in which a cartridge 740 may be positioned. The cartridge 740 may contain an anti-run-dry membrane 736 with a generally tubular shape, which may have a configuration similar to that of the anti-run-dry membrane 500 of FIGS. 5A and 5B and/or that of the anti-run-dry membrane 550 of FIGS. 5C and 5D.

The cartridge 740 may be designed to drop into the opening defined by the shelf 726 in order to act as a second piece of the drip unit 704, in cooperation with the exterior wall 720. The cartridge 740 may have an outer wall 742, which may retain the anti-run-dry membrane 736. The outer wall 742 may have a plurality of slots 744 extending longitudinally along its length. The outer wall 742 may have a solid top 746 that is substantially impermeable to the liquid 122. Alternatively, the solid top 746 may be replaced with an anti-run-dry membrane (not shown) like that of the anti-run-dry membrane 736, but with a shape that has a generally circular periphery (such as a generally circular or domed shape). The cartridge 740 may also have a tubing interface 748 designed to be connected to the first end 140 of the tubing 106.

In the configuration shown in FIG. 7, the liquid 122 may flow through the cartridge 740 to reach the tubing 106 via the tubing interface 748. Flow of the liquid 122 may be as indicated by the arrows 770. The liquid 122 may flow from the drip chamber 734, downward through the slots 744 of the cartridge 740 to reach the anti-run-dry membrane 736. The liquid 122 may then pass through the anti-run-dry membrane 736, and into the interior of the cartridge 740. The liquid 122 may then flow out of the cartridge 740 through the tubing interface 748 to reach the first end 140 of the tubing 106.

In yet other alternative embodiments, an anti-run-dry membrane may be retained within a drip unit without the need for a cartridge. In such a case, the anti-run-dry membrane may be retained directly by various features on the interior of the drip chamber. One such embodiment will be shown and described in connection with FIG. 8.

Figure 8:
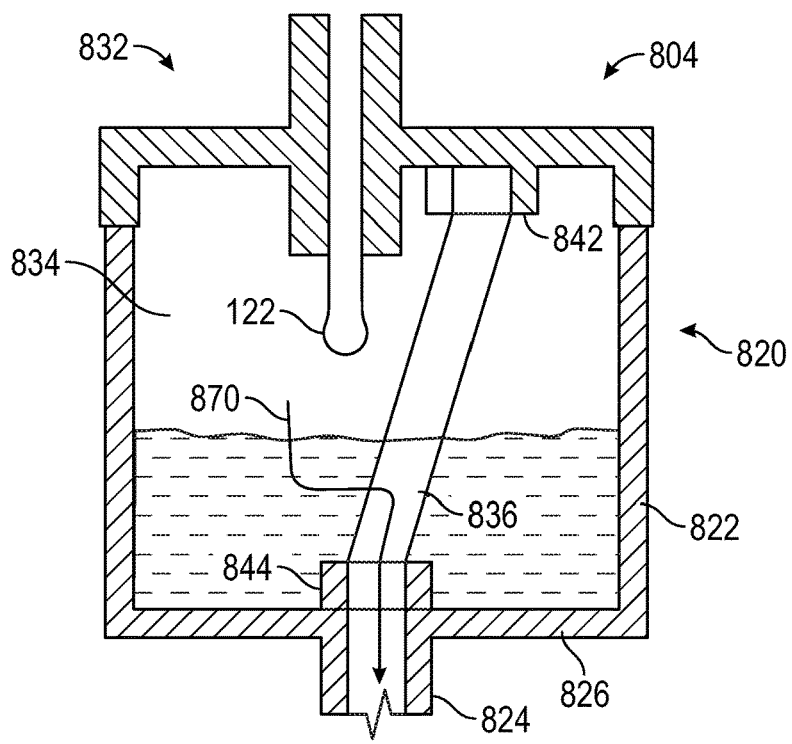
FIG. 8 is a front elevation, section view of a drip unit according to another alternative embodiment.

Referring to FIG. 8, a front elevation, section view illustrates a drip unit 804 according to another alternative embodiment. The drip unit 804 may have a drip feature 832 that delivers the liquid 122 to the interior of the drip unit 804, for example, in the form of drops. The drip unit 804 may have an exterior wall 820 that generally defines a drip chamber 834 to contain the liquid 122. The exterior wall 820 may have a peripheral portion 822 with a generally tubular and/or frustoconical shape, and a tubing interface 824 positioned at the bottom of the peripheral portion 822 and joined to the peripheral portion 822 by a bottom portion 826.

The drip chamber 834 may contain an anti-run-dry membrane 836 with a generally tubular shape, which may have a configuration similar to that of the anti-run-dry membrane 500 of FIGS. 5A and 5B and/or that of the anti-run-dry membrane 550 of FIGS. 5C and 5D. The anti-run-dry membrane 836 may be retained directly by the components that define the drip chamber 834. For example, the anti-run-dry membrane 836 may be retained at its lower end by the bottom portion 826 of the exterior wall 820, and at its upper end by the drip feature 832. The drip feature 832 may have a top membrane retainer 842 in the form of a tubular collar or the like, that retains the upper end of the anti-run-dry membrane 836. Similarly, the bottom portion 826 may have a bottom membrane retainer 844 in the form of a tubular collar or the like, that retains the lower end of the anti-run-dry membrane 836.

If desired, the top membrane retainer 842 may be offset from the central axis of the drip unit 804 as shown, so that the drip feature 832 can be configured to deliver the liquid 122 proximate the central axis. In alternative embodiments (not shown), the drip feature 832 may be configured to deliver the liquid 122 at a location offset from the central axis, and the top membrane retainer 842 may then be aligned with the bottom membrane retainer 844, along the central axis. Alternatively, the top membrane retainer 842 and the bottom membrane retainer 844 may be aligned with each other, but may both be displaced from the central axis. Such alternative configurations may position the anti-run-dry membrane 836 parallel to the central axis of the drip unit 804, rather than at the oblique angle illustrated in FIG. 8.

In any of those configurations, as in the configuration shown in FIG. 8, the liquid 122 may flow from the drip chamber 834 through the anti-run-dry membrane 836 to reach the interior of the anti-run-dry membrane 836. From the interior of the anti-run-dry membrane 836, the liquid 122 may flow downward and out of the drip unit 804 via the tubing interface 824. The liquid 122 may then pass into the first end 140 of the tubing 106. This motion of the liquid 122 is indicated by the arrow 870 in FIG. 8.

In yet other alternative embodiments, a cartridge may again be used to retain the anti-run-dry membrane, but such a cartridge may be secured to an element within the interior of the drip chamber of the drip unit. One example of such a configuration will be shown and described in connection with FIG. 9.

Referring to FIG. 9, a front elevation, section view illustrates a drip unit 904 according to yet another alternative embodiment. The drip unit 904 may have a drip feature 132 like that of FIG. 1. The drip unit 904 may have an exterior wall 920 that generally defines a drip chamber 934 to contain the liquid 122. The exterior wall 920 may have a peripheral portion 922 with a generally tubular and/or frustoconical shape, and a tubing interface 924 positioned below the peripheral portion 922 and designed to be connected to the first end 140 of the tubing 106. The exterior wall 920 may have a bottom portion 926 positioned to define a junction between the peripheral portion 922 and the tubing interface 924. The bottom portion 926 may be shaped to define a retention feature 928.

The drip unit 904 of FIG. 9 may contain an anti-run-dry membrane 936 with a generally tubular shape, which may have a configuration similar to that of the anti-run-dry membrane 500 of FIGS. 5A and 5B and/or that of the anti-run-dry membrane 550 of FIGS. 5C and 5D. The anti-run-dry membrane 936 may be retained in a cartridge 940, which may be formed separately from the exterior wall 920 and installed to rest on the bottom portion 926 of the exterior wall 920. The cartridge 940 may have an outer wall 942 with a plurality of slots 944 extending longitudinally along its length. The outer wall 942 may have a solid top 946 that is substantially impermeable to the liquid 122. Alternatively, the solid top 946 may be replaced with an anti-run-dry membrane (not shown) like that of the anti-run-dry membrane 936, but with a shape that has a generally circular periphery (such as a generally circular or domed shape).

The cartridge 940 may also have a bottom portion 948 with a retention feature 950 that mates with the retention feature 928 of the bottom portion 926 of the exterior wall 920. In the exemplary embodiment of FIG. 9, the retention feature 928 and the retention feature 950 both have frustoconical shapes that may simply fit together, allowing the cartridge 940 to be removably registered on the bottom portion 926 of the exterior wall 920. If desired, various attachment methods, such as welding, RF welding, chemical bonding, adhesive bonding, application of one or more mechanical fasteners and/or the like may be used to secure the cartridge 940 to the bottom portion 926.

In the configuration shown in FIG. 9, the liquid 122 may flow through the cartridge 940 to reach the tubing 106 via the tubing interface 924. Flow of the liquid 122 may be as indicated by the arrows 970. The liquid 122 may flow from the drip chamber 934, through the anti-run-dry membrane 936, and into the cartridge 940 through the slots 944 of the outer wall 942. From the interior of the cartridge 940, the liquid 122 may flow downward into the outer wall 942, and thence into the first end 140 of the tubing 106.

In yet other alternative embodiments, an anti-run-dry membrane may have a nonplanar shape that is not a tubular shape. In some embodiments, an anti-run-dry membrane may have a shape formed by deformation of the anti-run-dry membrane. For example, an anti-run-dry membrane may initially be in a planar configuration, but may be deformed through the application of one or more manufacturing processes, to take on a dome shape or other nonplanar shape. One example of such an embodiment will be shown and described in connection with FIGS. 10A and 10B.

Referring to FIGS. 10A and 10B, front elevation, section views illustrate a drip unit 1004 with an anti-run-dry membrane 1036 according to still another alternative embodiment, prior to and after shaping of the anti-run-dry membrane 1036, respectively. The drip unit 1004 may have a drip feature 132 like that of FIG. 1. The drip unit 1004 may have an exterior wall 1020 that generally defines a drip chamber 1034 to contain the liquid 122. The exterior wall 1020 may have a peripheral portion 1022 with a generally tubular and/or frustoconical shape, and a tubing interface 1024 positioned below the peripheral portion 1022 and designed to be connected to the first end 140 of the tubing 106. The exterior wall 1020 may have a shelf 1026 positioned to define a junction between the peripheral portion 1022 and the tubing interface 1024. A plurality of standoffs 1042 may be positioned below and interior to the shelf 1026.

Referring specifically to FIG. 10A, the anti-run-dry membrane 1036 may initially have a generally planar, circular shape, as shown. A manufacturing process may be used to increase the surface area of the anti-run-dry membrane 1036 by stretching the anti-run-dry membrane 1036 from its planar shape to a nonplanar shape. The anti-run-dry membrane 1036 may optionally be deformed in-situ by applying the manufacturing process with the anti-run-dry membrane 1036 in-place within the drip chamber 1034. Various processes, such as stamping, thermo-forming, and the like may be applied to the anti-run-dry membrane 1036 to stretch it into the configuration shown in FIG. 10B.

Referring now to FIG. 10B, the anti-run-dry membrane 1036 is illustrated after application of the manufacturing process to stretch it. As shown, the anti-run-dry membrane 1036 may have a generally domed configuration, with a profile limited by the standoffs 1042. The standoffs 1042 may help to ensure that the anti-run-dry membrane 1036 is sufficiently displaced from the tubing interface 1024 adjacent to the anti-run-dry membrane 1036, to enable the liquid 122 to flow relatively freely through the tubing interface 1024 and ensure that the vast majority of the surface area of the anti-run-dry membrane 1036 is not occluded by any portion of the exterior wall 1020.

The anti-run-dry membrane 1036 may have pores (not shown) like the pores 138 of the anti-run-dry membrane 136 of FIG. 1. If desired, the anti-run-dry membrane 1036 may be initially formed with pores smaller than those that are to exist in the anti-run-dry membrane 1036 in its final, stretched form. Thus, in the configuration of FIG. 10A, the anti-run-dry membrane 1036 may have pores that are smaller than desired. Then, as the manufacturing process is applied to stretch the anti-run-dry membrane 1036, the pores may also stretch into the desired size. Hence, in FIG. 10B, the anti-run-dry membrane 1036 may have pores with the desired size. Notably, such stretching may stretch the pores into a different shape than that in which they were originally formed. For example, pores initially formed with a circular cross sectional shape may be stretched to have elliptical and/or oval shapes or the tortuosity of the pore shape may be increased.

In some embodiments, an anti-run-dry membrane may be stretched, not by a manufacturing process, but by the flow of the liquid 122 through the anti-run-dry membrane or the weight of the liquid column. One example of such an embodiment will be shown and described in connection with FIGS. 11A and 11B.

Figure 11A:
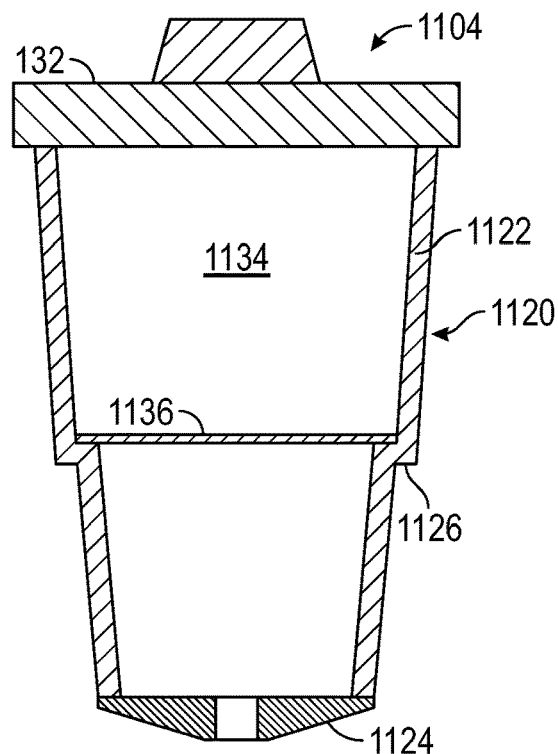
FIGS. 11A and 11B are front elevation, section views of a drip unit according to still another alternative embodiment, with no significant liquid flow, and with liquid flow incident to priming or use of the intravenous delivery system, respectively.
Figure 11B:
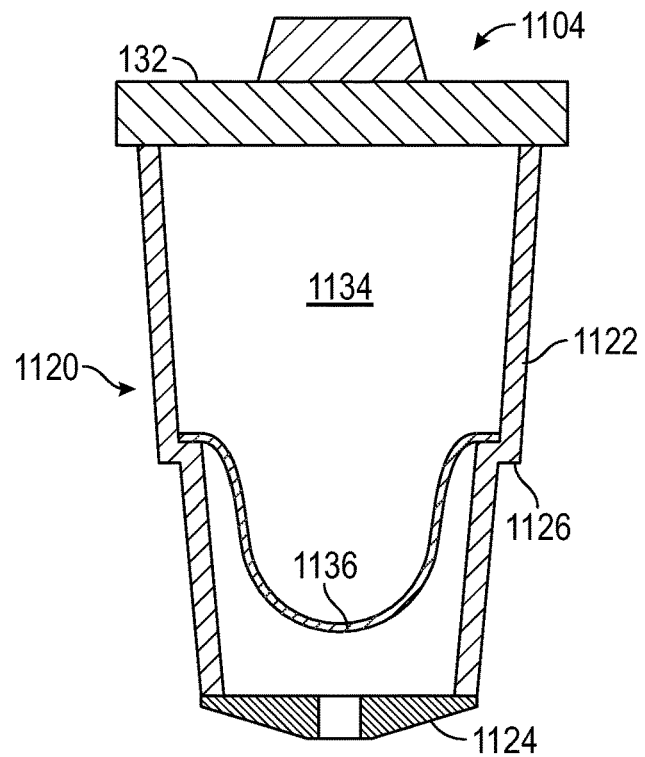

Referring to FIGS. 11A and 11B, front elevation, section views illustrate a drip unit 1104 according to still another alternative embodiment, with no significant liquid flow, and with liquid flow incident to priming or use of the intravenous delivery system, respectively. The drip unit 1104 may have a drip feature 132 like that of FIG. 1. The drip unit 1104 may have an exterior wall 1120 that generally defines a drip chamber 1134 to contain the liquid 122. The exterior wall 1120 may have a peripheral portion 1122 with a generally tubular and/or frustoconical shape, and a tubing interface 1124 positioned below the peripheral portion 1122 and designed to be connected to the first end 140 of the tubing 106. The exterior wall 1120 may have a shelf 1126 positioned to define a junction between the peripheral portion 1122 and the tubing interface 1124.

Referring specifically to FIG. 11A, the anti-run-dry membrane 1136 initially have a generally planar, circular shape, as shown, in the absence of significant flow of the liquid 122 through the anti-run-dry membrane 1136. The anti-run-dry membrane 1136 may have a relatively low thickness that permits the anti-run-dry membrane 1136 to stretch relatively easily in response to application of a pressure gradient across the anti-run-dry membrane 1136. Such a pressure gradient will exist when the liquid 122 begins to flow across the anti-run-dry membrane 1136. Hence, when the liquid 122 flows, as during priming of the intravenous delivery system 100 and/or use of the intravenous delivery system 100 to deliver the liquid 122 to the patient, the anti-run-dry membrane 1136 may stretch and expand into the cavity defined within the tubing interface 1124, which may be sized to accommodate the anti-run-dry membrane 1136. If desired, standoffs (not shown) like the standoff 1042 of FIGS. 10A and 10B may optionally be used.

Referring now to FIG. 11B, the anti-run-dry membrane 1136 is illustrated during significant flow of the liquid 122 through the anti-run-dry membrane 1136. As shown, the anti-run-dry membrane 1136 may have a generally domed configuration. The deformation of the anti-run-dry membrane 1136 may be extreme. In some embodiments, the material and geometry of the anti-run-dry membrane 1136 may be selected such that the deformation of the anti-run-dry membrane 1136 remains within the elastic limits of the material of which the anti-run-dry membrane 1136 is formed. Alternatively, the anti-run-dry membrane 1136 may be made such that plastic deformation occurs during flow of the liquid 122 through the anti-run-dry membrane 1136.

The anti-run-dry membrane 1136 may have pores (not shown) like the pores 138 of the anti-run-dry membrane 136 of FIG. 1. If desired, the anti-run-dry membrane 1136 may, in the generally unstretched configuration of FIG. 11A, have pores smaller than those that exist in the anti-run-dry membrane 1136 during flow of the liquid 122 through the anti-run-dry membrane 1136. Once the liquid 122 has stopped flowing through the anti-run-dry membrane 1136, some pressure gradient may still exist. Thus, the anti-run-dry membrane 1136 may remain in the configuration of FIG. 11B, or in a configuration between those of FIGS. 11A and 11B, reflecting the existence of a reduced pressure gradient. The pores of the anti-run-dry membrane 1136 may be sized such that the pores stretch to the size needed to raise the bubble point of the anti-run-dry membrane 1136 to the level needed to restrict airflow into the column of the liquid 122 below the anti-run-dry membrane 1136 when the liquid 122 is no longer flowing, but some pressure gradient still exists.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. An intravenous delivery system comprising:
    a liquid source containing a liquid;
    tubing comprising:
        a first end connectable to the liquid source to receive the liquid from the liquid source; and
        a second end connectable to an intravenous access unit that delivers the liquid to a patient;
    an anti-run-dry membrane positioned such that the liquid, flowing from the liquid source to the tubing, passes through the anti-run-dry membrane, wherein the anti-run-dry membrane comprises a plurality of pores through which the liquid flows, wherein the anti-run-dry membrane is formed of a hydrophilic material configured to resist passage of air through the pores; and
    a bubble point raising component configured to raise a bubble point of the anti-run-dry membrane, wherein the bubble point raising component comprises a liquid cooling unit that cools the liquid before the liquid contacts the anti-run-dry membrane to raise the bubble point of the anti-run-dry membrane.

2. The intravenous delivery system of claim 1, wherein the anti-run-dry membrane is formed of a membrane material having a membrane surface energy, wherein the bubble point raising component comprises a coating applied to the anti-run-dry membrane, wherein the coating is formed of a coating material comprising a coating surface energy higher than the membrane surface energy.

3. The intravenous delivery system of claim 1, wherein the anti-run-dry membrane is formed primarily of a membrane material having a membrane surface energy, wherein the bubble point raising component comprises an additive added to the membrane material prior to formation of the anti-run-dry membrane, wherein the additive is formed of an additive material comprising an additive surface energy higher than the membrane surface energy.

4. The intravenous delivery system of claim 1, wherein the anti-run-dry membrane is formed of a hydrophilic material, wherein the anti-run-dry membrane comprises a roughened surface finish that increases wettability of the anti-run-dry membrane.

5. The intravenous delivery system of claim 1, wherein, during flow of the liquid through the anti-run-dry membrane toward the tubing, the anti-run-dry membrane comprises a nonplanar shape.

6. The intravenous delivery system of claim 5, wherein the nonplanar shape comprises a domed shape.

7. The intravenous delivery system of claim 5, wherein the nonplanar shape comprises at least one fold defining an angle between two adjacent surfaces of the anti-run-dry membrane.

8. The intravenous delivery system of claim 5, wherein the nonplanar shape comprises a generally tubular shape.

9. The intravenous delivery system of claim 5, wherein the anti-run-dry membrane comprises a membrane material that has been plastically deformed by application of a manufacturing process configured to stretch the anti-run-dry membrane into the nonplanar shape.

10. The intravenous delivery system of claim 5, wherein, during a condition in which the liquid is not flowing through the anti-run-dry membrane in any particular direction, the anti-run-dry membrane is in a first configuration in which the anti-run-dry membrane has a first surface area; wherein, during flow of the liquid through the anti-run-dry membrane toward the tubing or when supporting a fluid column, the anti-run-dry membrane is in a second configuration in which the anti-run-dry membrane comprises the nonplanar shape has a second surface area significantly larger than the first surface area.

11. The intravenous delivery system of claim 5, wherein of the effective pore size is less than 3 micrometers.

12. The intravenous delivery system of claim 11, wherein the anti-run-dry membrane comprises a thickness of less than 90 micrometers.

13. The intravenous delivery system of claim 1, further comprising:
a drip unit connectable to the liquid source to receive the liquid, wherein the drip unit is further connectable to the first end of the tubing to deliver the liquid to the tubing, the drip unit comprising a drip chamber into which the liquid flows via gravity feed;
wherein the anti-run-dry membrane is positioned within the drip chamber such that the liquid passes through the anti-run-dry membrane prior to passing into the first end of the tubing.

14. A method for using an intravenous delivery system, the intravenous delivery system comprising a liquid source, tubing, and an anti-run-dry membrane, and a bubble point raising component, the tubing comprising a first end connected to the liquid source and a second end connectable to an intravenous access unit that delivers the liquid to a patient, the method comprising:
priming the intravenous delivery system by gravity feeding liquid from the liquid source through the anti-run-dry membrane and into the tubing;
delivering the liquid to the patient via the intravenous access unit;
substantially stopping flow of the liquid from the liquid source;
in response to substantially stopping flow of the liquid from the liquid source, developing a column of the liquid below the anti-run-dry membrane; and
with the bubble point raising component, substantially preventing passage of air into the column of the liquid through the anti-run-dry membrane.

15. The method of claim 14, wherein the anti-run-dry membrane is formed of a membrane material having a membrane surface energy, wherein the bubble point raising component comprises a coating applied to the anti-run-dry membrane, wherein the coating is formed of a coating material comprising a coating surface energy higher than the membrane surface energy;
wherein substantially preventing passage of air into the column of the liquid through the anti-run-dry membrane with the bubble point raising component comprises increasing a bubble point of the anti-run-dry membrane with the coating.

16. The method of claim 14, wherein the anti-run-dry membrane is formed primarily of a membrane material having a membrane surface energy, wherein the bubble point raising component comprises an additive added to the membrane material prior to formation of the anti-run-dry membrane, wherein the additive is formed of an additive material comprising an additive surface energy higher than the membrane surface energy;
wherein substantially preventing passage of air into the column of the liquid through the anti-run-dry membrane with the bubble point raising component comprises increasing a bubble point of the anti-run-dry membrane with the additive.

17. The method housing of claim 14, wherein, during flow of the liquid through the anti-run-dry membrane toward the tubing, the anti-run-dry membrane comprises at least one nonplanar shape selected from the group consisting of:
a domed shape;
a folded shape comprising at least one fold defining an angle between two adjacent surfaces of the anti-run-dry membrane; and
a generally tubular shape.

18. The method housing of claim 14, wherein priming the intravenous delivery system comprises moving the anti-run-dry membrane from a first configuration in which the anti-run-dry membrane has a first surface area, to a second configuration in which the anti-run-dry membrane comprises a nonplanar shape has a second surface area significantly larger than the first surface area.

19. An intravenous delivery system comprising:
a liquid source containing a liquid;
tubing comprising:
a first end connectable to the liquid source to receive the liquid from the liquid source; and
a second end connectable to an intravenous access unit that delivers the liquid to a patient;
a drip unit comprising a drip chamber that receives the liquid from the liquid source and delivers the liquid to the first end of the tubing, wherein the drip unit further comprises an anti-run-dry membrane formed of a hydrophilic material and positioned within the chamber; and
a bubble point raising component configured to raise a bubble point of the anti-run-dry membrane;
wherein the anti-run-dry membrane has a thickness of less than 90 micrometers, the anti-run-dry membrane comprises at least one nonplanar shape selected from the group consisting of:
a domed shape;
a folded shape comprising at least one fold defining an acute angle between two adjacent surfaces of the anti-run-dry membrane; and
a generally tubular shape;
wherein the anti-run-dry membrane comprises a plurality of pores through which the liquid flows, each of which is less than 3 micrometers in size; and
wherein the anti-run-dry membrane is formed of a membrane material having a membrane surface energy, wherein the bubble point raising component comprises a selection from the group consisting of:
a coating applied to the anti-run-dry membrane, wherein the coating is formed of a coating material comprising a coating surface energy higher than the membrane surface energy; and an additive added to the membrane material prior to formation of the anti-run-dry membrane, wherein the additive is formed of an additive material comprising an additive surface energy higher than the membrane surface energy.

\* \* \* \* \*